(12) United States Patent
Robertson et al.

(10) Patent No.: US 10,513,824 B2
(45) Date of Patent: Dec. 24, 2019

(54) METHOD FOR REDUCING PULP VISCOSITY IN PRODUCTION OF DISSOLVING PULP

(71) Applicant: Kemira Oyj, Helsinki (FI)

(72) Inventors: Leif Robertson, Parainen (FI); Veli-Matti Vuorenpalo, Espoo (FI); Jonas Konn, Espoo (FI); Kaisa Kaski, Vaasa (FI)

(73) Assignee: Kemira Oyj, Helsinki (FI)

( * ) Notice: Subject to any disclaimer, the term of this patent is extended or adjusted under 35 U.S.C. 154(b) by 59 days.

(21) Appl. No.: 15/576,845

(22) PCT Filed: May 26, 2016

(86) PCT No.: PCT/FI2016/050365
§ 371 (c)(1),
(2) Date: Nov. 26, 2017

(87) PCT Pub. No.: WO2016/189205
PCT Pub. Date: Dec. 1, 2016

(65) Prior Publication Data
US 2018/0163344 A1    Jun. 14, 2018

(30) Foreign Application Priority Data

May 27, 2015    (FI) .................................... 20155400

(51) Int. Cl.
| | |
|---|---|
| *D21C 9/00* | (2006.01) |
| *D21C 9/10* | (2006.01) |
| *D21C 3/04* | (2006.01) |
| *D21C 3/22* | (2006.01) |
| *D21C 3/00* | (2006.01) |
| *C07C 409/26* | (2006.01) |
| *D21C 1/02* | (2006.01) |
| *D21C 3/02* | (2006.01) |
| *D21C 3/26* | (2006.01) |

(52) U.S. Cl.
CPC ............ *D21C 9/004* (2013.01); *C07C 409/26* (2013.01); *D21C 1/02* (2013.01); *D21C 3/00* (2013.01); *D21C 3/022* (2013.01); *D21C 3/04* (2013.01); *D21C 3/222* (2013.01); *D21C 3/26* (2013.01); *D21C 9/10* (2013.01); *D21C 9/1036* (2013.01); *D21C 9/1052* (2013.01)

(58) Field of Classification Search
CPC ........ D21H 2/132; D21H 5/148; D21H 17/25; D21H 3/18; D21H 27/16; D21H 21/32
See application file for complete search history.

(56) References Cited

U.S. PATENT DOCUMENTS

| | | | | |
|---|---|---|---|---|
| 3,632,469 | A * | 1/1972 | Wilder | D21C 9/142 162/25 |
| 4,013,506 | A * | 3/1977 | Histed | D21C 9/1052 162/238 |
| 6,136,041 | A * | 10/2000 | Jaschinski | D21C 9/1036 162/78 |
| 2003/0150574 | A1* | 8/2003 | Paren | D21H 17/14 162/158 |
| 2006/0199742 | A1 | 9/2006 | Arisz et al. | |
| 2009/0221704 | A1* | 9/2009 | Aksela | A01N 37/02 514/557 |

FOREIGN PATENT DOCUMENTS

| | | | |
|---|---|---|---|
| CN | 103122594 A1 | 3/2014 | |
| EP | 0441113 A1 | 8/1991 | |
| EP | 2573259 A1 | 3/2013 | |
| EP | 2609990 A1 * | 7/2013 | ........... B01D 61/025 |
| JP | 2000212883 A | 8/2000 | |
| WO | WO-9932710 A1 * | 7/1999 | ............ D21C 9/166 |
| WO | 00077301 A1 | 12/2000 | |
| WO | 20120175815 A1 | 12/2012 | |
| WO | 2014041251 A1 | 3/2014 | |

OTHER PUBLICATIONS

Cepi, Pulp and Paper Industry—Definitions and Concepts, Dec. 2014, Cepi, p. 13-14 (Year: 2014).*
Durbak, Irene, Dissolving pulp industry: Market trends, Sep. 1993, U.S. Department of Agriculture, p. 2. (Year: 1993).*
Kemira, Annual Report 2012, 2012, Kemira, p. 1-3 of the pdf document. (Year: 2012).*
Janne Vehmaa, Manufacturing of dissolcing hardwood and softwood pulp with continuous cooking and novel fiberline technology, 2012, Andritz Pulp and Paper, whole document (Year: 2012).*
Finnish Patent and Registration Office, Search Report, FI20155400, dated Jan. 27, 2016.
Abad, S. et al, Evalutation of Eucalyptus globulus Wood Processing in Media Made up of Formic Acid, Water, and Hydrogen Peroxide for Dissolving Pulp Production, Ind. Eng. Chem. Res. (2001), vol. 40, 413-419. Whole document.
Finnish Patent and Registration Office, Search Report, FI20155400, Principal Examiner Timo Kallio, dated Jan. 27, 2016, 2 pages.

* cited by examiner

*Primary Examiner* — Anthony Calandra
*Assistant Examiner* — Elisa Vera
(74) *Attorney, Agent, or Firm* — Berggren LLP

(57) ABSTRACT

The invention relates to a method for reducing pulp viscosity in production of dissolving pulp. The method comprises producing cellulose pulp, whereby the obtained cellulose pulp has a cellulose content of at least 90%, and bleaching the obtained cellulose pulp. The cellulose pulp is treated after bleaching with performic acid.

13 Claims, No Drawings

METHOD FOR REDUCING PULP VISCOSITY IN PRODUCTION OF DISSOLVING PULP

PRIORITY

This application is a U.S national application of PCT-application PCT/FI2016/050365 filed on May 26, 2016 and claiming priority of Finnish application FI 20155400 filed on May 27, 2015, the contents of both of which are incorporated herein by reference.

The invention relates to a method for reducing pulp viscosity in production of dissolving pulp according to preambles of enclosed independent claim.

Dissolving pulp is bleached cellulose pulp which is manufactured in a chemical pulping process, where chips of debarked wood are cooked with a mixture of cooking chemicals in order to remove lignin, extractives and hemicelluloses from the pulp. After cooking the pulp is washed, bleached and dried. The obtained dissolving pulp has a high cellulose content and high level of brightness. Wood or cotton linters may be used as raw material in the process.

Dissolving pulp is not used for producing bulk paper or board products but for end uses which have special requirements for chemical purity and low hemicellulose content of the pulp. Dissolving pulp is dissolved either by a solvent or by derivatisation into homogenous solution, which can be used for spinning of textile fibres, for production of derivatised celluloses, such as cellulose triacetate, or for production of cellulose ethers, such as carboxymethyl cellulose.

The important quality parameters in producing dissolving pulp are the high purity, i.e. high cellulose content and brightness, as well as the low viscosity of the pulp. If the viscosity of the pulp is too high, the price of the produced pulp decreases. Therefore the viscosity of the pulp is one of the key interests in the production. Traditionally the viscosity of the pulp is controlled by addition of hypochlorite in a separate bleaching stage. However, when the use of chlorine compounds in pulp production has been declining due to environmental concerns, there is a constant need for effective solutions for controlling the viscosity of the produced pulp.

The object of the present invention is to minimize or even eliminate the disadvantages existing in the prior art.

One object of the present invention is to provide an effective method for controlling the viscosity of the dissolving pulp.

These objects are achieved by the features disclosed in the independent claim.

The invention is defined by the features of the enclosed independent claim. Some preferred embodiments of the present invention are presented in the dependent claims.

Typical method according to the present invention for reducing pulp viscosity in production of dissolving pulp comprises
  producing cellulose pulp, whereby the obtained cellulose pulp has a cellulose content of at least 90%,
  bleaching the obtained cellulose pulp, and
  treating the obtained cellulose pulp after bleaching with performic acid.

Now it has been surprisingly found that an addition of performic acid to bleached pulp after the bleaching stage produces reduction in pulp viscosity. Even relatively small dosages of performic acid are able to considerably reduce the viscosity of the dissolving pulp. Furthermore, performic acid is a reaction product of formic acid and hydrogen peroxide and it is fully biodegradable and corrosion safe. Thus the use of performic acid is advantageous, as it or its degradation products do not harm the environment or the process equipment.

Performic acid, $CH_2O_3$, is used in the invention as an aqueous solution. Typically the performic acid has a concentration at least 10%, calculated as weight to volume, typically around 13.5%, calculated as weight to volume. Preferably the aqueous performic acid solution is used as an equilibrium solution.

Typically the pulp is obtained from the bleaching as aqueous slurry, which has a consistency of 5-15%, preferably 7-12%, calculated as dry content. The bleaching may comprise one or several bleaching steps, where the pulp is brought into contact with bleaching chemical(s). The pulp may be treated with performic acid directly and immediately after the end of the last bleaching step. This means that performic acid is added to the aqueous pulp after the last bleaching step.

According to one embodiment of the invention performic acid is used in amount of 0.1-7 kg/ton dry pulp, preferably 0.5-5 kg/ton dry pulp, more preferably 1-3 kg/ton dry pulp. The dose is given as 100% performic acid.

The added performic acid does not provide significant improvement in brightness of the pulp. Thus the function of the performic acid is not to improve the brightness of the pulp but to reduce the viscosity. The viscosity decrease may be at least 30 $dm^3/kg$, preferably at least 50 $dm^3/kg$, measured according to standard CAN-CM 15:99 or standard ISO 5351. The viscosity decrease is understood as the difference between the viscosity value of the pulp measured before the treatment with performic acid and the viscosity value of the pulp measured after the treatment with performic acid. The brightness change is typically less than 2% ISO, preferably less than 1% ISO, measured according to standards ISO 3688, ISO 2470. The brightness change is the difference between the brightness of the pulp measured before the treatment with performic acid and the brightness of the pulp measured after the treatment with performic acid.

The pH of the pulp slurry during the treatment with performic acid is at least 5, preferably at least 6. Preferably the pH during the treatment with performic acid is less than 11, preferably less than 10. Typically the pH during the treatment with performic acid may be in the range of 5-10, preferably 6-8. Preferably pH of the pulp slurry does not significantly change during the treatment with performic acid, normally the pH change is less than one pH unit.

The temperature during performic acid treatment may be in the range of 30-100° C., preferably 40-70° C. Thus no additional heating or cooling of the pulp slurry is needed for the performic acid treatment, and the pulp slurry can be treated directly and immediately after the end of bleaching. In other words, the method is preferably free from additional heating or cooling of the pulp before the treatment with performic acid.

According to one preferable embodiment of the invention the performic acid is produced on-site and led directly to the performic acid treatment stage. This means that the produced performic acid is used directly for treating the cellulose pulp after bleaching. A preparation unit for performic acid, which is suitable for use in the present invention, has been designed by Kemira Oyj, Finland. Performic acid may thus be prepared in the immediate vicinity of the process location where it is added to the pulp slurry. This guarantees the high chemical efficiency of the performic acid. Performic acid is led to the process location through suitable connections and fed to a desired flow of pulp slurry by using suitable feeding means. Performic acid may be fed directly to the process flow of pulp slurry, and the mixing of the performic acid is achieved by the turbulent flow.

According to one embodiment of the invention, in addition of performic acid it is also possible to add distilled peracetic acid to the pulp slurry after bleaching step. Distilled peracetic acid may be added to the pulp slurry in amount of 0.01-30 kg/ton dry pulp, preferably 10-20 kg/ton dry pulp. The addition of distilled peracetic acid can be done before or after the addition of performic acid, i.e. before or after the treatment of pulp with performic acid. Distilled peracetic acid provides a delignifying and/or brightening effect, and thus forms a post-bleaching step, which can be used to reduce variations in brightness of the pulp, or combat post-bleach yellowing of the pulp.

The described method can be used to reduce the viscosity of dissolving cellulose pulp, which is produced by a kraft process, optionally with a prehydrolysis step. During the prehydrolysis step at least a part, preferably a major part, of the hemicelluloses in the cellulose containing raw material are degraded and/or dissolved. After the pre-hydrolysis step the raw material is further treated in the kraft process with sodium hydroxide or with an aqueous mixture of sodium hydroxide and sodium sulfide, whereby lignin is degraded and solubilized. This leads to liberation of cellulose fibres. Alternatively the method according to the present invention can be used to reduce the viscosity of dissolving cellulose pulp, which is produced by using acid sulphite pulping process employing bisulphite solution as cooking liquor. The sulphite process may also comprise a prehydrolysis step for dissolving hemicelluloses.

The cellulose pulp which is treated with performic acid has a cellulose content of at least 92%, preferably at least 95%.

According to one embodiment of the invention the viscosity of the pulp after the bleaching, i.e. after the last bleaching step, is measured, and the pulp is treated with performic acid in case the viscosity value of the pulp is higher than a predetermined viscosity value. It is also possible to adjust the amount of performic acid which is used for treating the pulp on basis of the obtained or measured viscosity value.

According to another embodiment of the invention the cellulose pulp is treated by continuous addition of performic acid to the pulp after the bleaching. The addition of performic acid may be fully automated.

EXPERIMENTAL

Some embodiments of the invention are more closely described in the following non-limiting example.

Example 1

Off-spec dissolving kraft mill pulp was subjected separately to a viscosity reducing treatment after bleaching. The viscosity reducing step was performed at temperature of 60° C., residence time 120 min. The pulp consistency was 10% and used peracid dose was 2 kg/ton dry pulp. pH level of the pulp was 8. Two different peracids were tested, namely, performic acid (PFA) and peracetic acid (PAA).

The results of Example 1 are shown in Table 1.

TABLE 1

| Results of Example 1. | | | |
|---|---|---|---|
| | Reference Sample | Sample 2 | Sample 3 |
| Used peracid | — | PAA | PFA |
| Final-pH | 8 | 5.7 | 7.0 |
| Residual-PAA, kg/ton pulp | — | 0.69 | 0 |
| Viscosity, dm$^3$/kg | 507 | 470 | 447 |
| Brightness, % ISO (standard ISO 2470) | 90.4 | 91.3 | 90.8 |
| Yellowness | 5.5 | 5.1 | 5.4 |
| Whiteness CIE D65/10+UV (standard CIE 15:2004) | 80.1 | 81.8 | 80.9 |
| L* | 97.8 | 98 | 97.9 |
| a* | −0.36 | −0.32 | −0.28 |
| b* | 3.23 | 2.97 | 3.13 |

It can be seen from Table 1 that treatment of pulp with performic acid reduced the viscosity by 60 dm$^3$/kg, which is more than enough to turn an off-spec pulp into an in-spec pulp. The same significant viscosity reduction could not be observed when peracetic acid was used.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method for reducing pulp viscosity in production of dissolving pulp, the method comprising:
   producing a cellulose pulp having a cellulose content of at least 90%;
   bleaching the obtained cellulose pulp;
   and
   decreasing
   the viscosity of the bleached pulp by treating the bleached pulp with performic acid, while at the same time, keeping a brightness change of the pulp to less than 1% ISO,
   wherein the brightness change is a difference between a brightness of the pulp measured before a treatment with the performic acid and a brightness of the pulp measured after a treatment with the performic acid, and
   wherein the pH during treatment with the performic acid is in a range between 6-8.

2. The method according to claim 1, wherein performic acid is used in amount of 0.1-7 kg/ton pulp.

3. The method according to claim 1, wherein during the treatment with performic acid pH of the pulp changes less than one pH unit.

4. The method according to claim 1, wherein the temperature during the treatment with performic acid is in a range of 30-100° C.

5. The method according to claim 1, wherein the method is free from additional heating or cooling of the cellulose pulp before the treatment with performic acid.

6. The method according to claim 1, wherein the pulp is treated with performic acid directly and immediately after the end of the bleaching step.

7. The method according to claim 1, wherein the bleached pulp has a consistency of 5-15%, calculated as dry content.

8. The method according to claim 1, wherein the performic acid is produced on-site and used directly for treating the obtained bleached cellulose pulp.

9. The method according to claim 1, wherein distilled peracetic acid is added to the pulp after the bleaching in amount of 0.01-30 kg/ton dry pulp.

10. The method according to claim 1, wherein the obtained cellulose pulp is produced by a kraft process with a prehydrolysis step.

11. The method according to claim 1, wherein the obtained cellulose pulp, which is treated with performic acid, has a cellulose content of at least 92%.

12. The method according to claim 1, wherein the obtained bleached cellulose pulp is treated by continuous addition of performic acid to the pulp after the bleaching.

13. The method according to claim 1, wherein the viscosity decrease of the cellulose pulp is at least 30 dm$^3$/kg.

* * * * *